(12) United States Patent
Kusunose

(10) Patent No.: US 6,858,859 B2
(45) Date of Patent: Feb. 22, 2005

(54) OPTICALLY SCANNING APPARATUS AND DEFECT INSPECTION SYSTEM

(75) Inventor: Haruhiko Kusunose, Yokohama (JP)

(73) Assignee: Lasertec Corporation, Yokohama (JP)

(*) Notice: Subject to any disclaimer, the term of this patent is extended or adjusted under 35 U.S.C. 154(b) by 0 days.

(21) Appl. No.: 10/126,525

(22) Filed: Apr. 22, 2002

(65) Prior Publication Data

US 2002/0162979 A1 Nov. 7, 2002

(30) Foreign Application Priority Data

May 2, 2001 (JP) ........................................ 2001-134956

(51) Int. Cl.$^7$ ............................................. G01N 21/88
(52) U.S. Cl. ............................... 250/559.45; 356/237.2
(58) Field of Search ................................ 348/125–126; 356/450–521, 237.2–237.5, 239.3, 239.7, 239.8, 399–401; 250/237 R, 237 G, 556, 559.4, 559.42, 559.44, 559.45, 559, 14, 559.17, 22

(56) References Cited

U.S. PATENT DOCUMENTS 5,774,222 A * 6/1998 Maeda et al. ............... 356/394
6,043,932 A * 3/2000 Kusunose .................... 359/368
6,208,411 B1 * 3/2001 Vaez-Iravani ............. 356/237.2
6,433,876 B1 * 8/2002 Kuhn ........................... 356/516

FOREIGN PATENT DOCUMENTS

JP    A 11-199031    7/1999

\* cited by examiner

Primary Examiner—David Porta
Assistant Examiner—Patrick J. Lee
(74) Attorney, Agent, or Firm—Oliff & Berridge, PLC

(57) ABSTRACT

An optically scanning apparatus and defect inspection system able to detect a defect with a high resolution and able to greatly shorten the inspection time. An radiation beam generated from a light source is converted to a light beam array of an m×n matrix by a two-dimensional diffraction grating. The light beams of the light beam array are focused into micro spots by an objective lens and projected on a sample. Therefore, a two-dimensional light spot array of an m×n matrix is formed on a sample. The sample stage rotates and moves rectilinearly in an r direction, so the sample surface is scanned by the m×n matrix of light spots. As a result, the sample surface is spirally scanned by a light beam of a belt shape of the scan width, so can be scanned at a high speed. Further, the beams reflected by the sample surface are received by light receiving elements separated by light blocking members, so a confocal optical system is formed and as a result the resolution of detection of defects becomes much higher.

27 Claims, 10 Drawing Sheets

OPTICALLY SCANNING APPARATUS AND DEFECT INSPECTION SYSTEM

BACKGROUND OF THE INVENTION

1. Field of the Invention

The present invention relates to an optically scanning apparatus for optically scanning the surface of a sample by m×n (m and n being natural numbers of 2 or more) number of sub beams and a defect inspection system for detecting a defect existing on the surface of a sample using this optically scanning apparatus.

2. Description of the Related Art

Along with the increasing miniaturization of LSIs (large scale integrations), there has been strong demand for development of a defect inspection system able to accurately detect micro defects existing on the surface of a semiconductor wafer, patterned wafer, mask blank, etc. In particular, there has been strong demand for development of a defect inspection system able to accurately detect micro defects since the manufacturing yield falls by a large margin when defects are present on a semiconductor wafer before processing for fabrication of semiconductor devices.

In the past, as a system for inspecting a semiconductor wafer for defects, there has been a defect inspection system using laser scattered light. In a defect inspection system using laser scattered light, the sample to be inspected for defects is placed on a rotating sample stage, a single laser beam is projected toward the sample, and the light scattered from the surface of the sample is detected to inspect for defects.

As another defect inspection system, there is known a defect inspection system disclosed in Japanese Unexamined Patent Publication (Kokai) No. 11-199031 previously proposed by the present assignee. In this known defect inspection system, a light beam generated from a laser light source is converted by a one-dimensional diffraction grating to n number of sub beams arranged in lines. The surface of the sample is raster scanned by these n number of sub beams. The light of the n number of sub beams reflected from the surface of the sample are received by a photosensor having n number of light receiving elements. The output signals of the light receiving elements are compared with each other to detect defects. A defect inspection system utilizing such sub beams uses a confocal optical system, so achieves a high resolution and can accurately defect micro defects of for example about 50 nm.

Summarizing the problem to be solved by the invention, a defect inspection system of the laser scattered light type places the sample on a rotating sample stage and projects a single laser beam toward the rotating sample, so the entire surface of the sample can be scanned in a relatively short time. Therefore, there is the effect that the inspection time can be shortened. The surface of a semiconductor wafer, however, has micro step differences or unevenness of an atomic level, so the intensity of the light scattered from the surface of a normal sample is too strong and scattered light due to defects present on the surface of the sample is difficult to differentiated from the light scattered from a normal surface. As a result, the resolution of detection of defects becomes low. In particular, in the case of a wafer annealed by hydrogen or a semiconductor wafer formed with an epitaxial layer on the surface, the surface of the wafer has surface roughness on an atomic level, so scattered light is produced not due to defects. To reduce the effects of this scattered light, the detection sensitivity has to be lowered and detection of micro defects of about 50 nm size becomes difficult.

On the other hand, a defect inspection system of the multi beam system uses a confocal optical system, so achieves a high resolution and can accurately detect defects of even about 50 nm size. Since it raster scans the surface of a sample by a plurality of light beams arranged in lines, however, a relatively long time is required to scan the entire surface of a sample and the inspection time becomes long.

SUMMARY OF THE INVENTION

An object of the present invention is to provide an optically scanning apparatus and defect inspection system able to greatly shorten the inspection time and obtain a high resolution.

Another object of the present invention is to provide a defect inspection system able to detect micro unevenness and defects with a high sensitivity.

In accordance with a first aspect of the present invention, there is provided an optically scanning apparatus comprising a light source for emitting a radiation beam; a two-dimensional diffraction grating for converting the radiation beam into a two-dimensional array of light beams arranged in an m×n matrix, where m and n are natural numbers or 2 or more; an objective lens for focusing m×n number of light beams into spots to form an array of light spots arranged in an m×n matrix on a sample to be inspected; a photosensor having an array of light receiving elements arranged in an m'×n' (m' and n' being natural numbers of 2 or more) matrix, the light receiving elements separated from each other and receiving beams reflected at the sample surface; a sample stage for supporting a sample to be inspected for defects; and a stage drive system having a rotational drive device for rotating the sample stage and a rectilinear movement device for moving the sample stage along an axis perpendicular to the rotational axis and making the sample stage move relative to the light spot array; wherein the sample surface being scanned by the two-dimensional light spot array arranged in an m×n matrix by making the sample and light spot array move relative to each other.

According to the present invention, a beam emitted from a light source is converted by a diffraction grating into an array of light beams arranged in an m×n matrix and these light beams are focused by an objective lens into light spots to form an array of light spots of an m×n matrix on the sample. The sample to be inspected for defects is supported on a sample stage and the sample stage is made to rotate and move rectilinearly along a radial direction perpendicular to the axis of rotation. Due to this, the sample to be inspected is scanned by m×n light spots and therefore the surface of the sample is scanned by a light beam of a broad width belt shape formed by the m×n number of light spots. As a result, the surface of the sample can be scanned at high speed and the inspection time can be greatly shortened. Further, in the present invention, the photosensor is comprises an array of light receiving elements arranged in a two-dimensional matrix and separated by light blocking member, so the optical system of the present invention forms a confocal optical system. As a result, flare due to fine step differences or unevenness present on the sample surface can be avoided and just the regularly reflected light from the light spots formed on the sample surface strikes the light receiving elements. Therefore, the influence of flare is eliminated and a high resolution optical system can be realized. As a result, the defect inspection system greatly reduced in inspection time and having an extremely high resolution can be achieved.

Further, in the optically scanning apparatus of the present invention, the relative movement between a light spot and sample is performed by the rotational movement and the rectilinear movement of the sample stage. Therefore, the optical system is fixed in place and the light beams propagate along the same position in the optical path without scanning. As a result, the light beams pass through the same position of the lens at all times, and thus significant effects can be obtained in that shading effects due to interference or aberration do not occur.

Preferably, the light spot array is formed so that the intervals between adjoining light spots become equal when projecting the m×n number of light spots formed on the sample on an axis of movement Lr of the rectilinear movement device projected on the sample stage. When scanning the sample surface by a two-dimensional beam array, it is necessary to prevent the light beams from overlapping each other in a direction perpendicular to the scan direction and to prevent the formation of gaps between adjoining light beams. To satisfy these requirements, the projections of the m×n number of light beams in a direction perpendicular to the scan direction are set to become equal in interval.

More preferably, an angle formed between an axis in a row direction of an m×n two-dimensional light spot array formed on the sample and an axis of movement Lr of the rectilinear movement device projected on the sample stage is θ, the interval between light spots in the row direction is P1, and the interval between spots in the column direction is P2, the light spot array is formed with respect to the axis of movement Lr of the rectilinear movement device so that the following equation is satisfied:

$$\tan \theta = (1/n) \times (P1/P2)$$

By forming the light spot array so that the condition defined by the above equation is satisfied, when projecting the m×n number of lights spots with respect to the axis of rectilinear movement Lr, it is possible to set the interval between light spots at equal intervals.

Alternatively, when the intervals P1 and P2 of the row direction and column direction between light spots of the light spot array formed on the sample are set so that P1=P2, the light spot array is formed with respect to the axis of movement Lr of the rectilinear movement device so that the following equation is satisfied:

$$\tan \theta = 1/n$$

Preferably, the sample stage moves rectilinearly by exactly a distance corresponding to a scan width while the sample stage rotates one time.

Preferably, a beam splitter is arranged in the light path between the light source and sample stage so as to separate the light beam propagating from the light source to the sample stage and the light beam propagating from the sample stage to the photosensor.

More preferably, an differential interference optical system is arranged in the light path between the beam splitter and object lens.

Still more preferably, the differential interference optical system is formed by a Nomarski prism.

Alternatively, a zoom lens system is arranged in the light path between the photosensor and beam splitter.

Preferably, the array of light receiving elements of the photosensor is formed by an array of separated photodiodes.

Preferably, the sample stage has a θ-stage able to rotate around an axis of rotation and an r-stage able to move along the axis of movement Lr, a first position detection device for detecting an angular position in a rotational direction is connected to the θ-stage, and a second position detection device for detecting a position in a direction of an axis of rectilinear movement is connected to the r-stage.

According to a second aspect of the present invention, there is provided a defect inspection system comprising a light source for emitting a radiation beam; a two-dimensional diffraction grating for converting the radiation beam into a two-dimensional array of light beams arranged in an m×n matrix, where m and n are natural numbers of 2 or more; an object lens for condensing m×n number of light beams into spots to form an array of light spots arranged in an m×n matrix on a sample to be inspected; a photosensor having an array of light receiving elements arranged in an m'×n' (m' and n' being natural numbers of 2 or more) matrix, the light receiving elements separated from each other and receiving beams reflected at the sample surface; a sample stage for supporting a sample to be inspected for defects; and a stage drive system having a rotational drive device for rotating the sample stage and a rectilinear movement device for moving the sample stage along an axis perpendicular to the rotational axis and making the sample stage move relative to the light spot array; and a defect detection system for detecting a defect present on a surface region of a sample based on an output signal from a light receiving element of the photosensor.

A light blocking plate is arranged at the pupil position present between the beam splitter and photosensor of the optical system and the light blocking plate is used to block one side of the light path in a direction corresponding to the scan direction on the same by the light beams. By arranging the light blocking plate at the pupil position and blocking one side of the light path, it is possible to detect height information of the sample surface at a higher sensitivity. In particular, it is possible to determine if the sample surface is recessed or projecting by the waveform of the output signals from the light receiving elements.

Preferably, wherein the two-dimensional diffraction grating converts the emitted beam into a two-dimensional beam array comprised of emitted light beams arranged at equal intervals in a row direction and column direction.

Preferably, the light spot array is formed so that the intervals between adjoining light spots become equal when projecting m×n number of light spots formed on the sample on an axis of movement Lr of the rectilinear movement device projected on the sample stage.

Preferably, when an angle formed between an axis in a row direction of an m×n two-dimensional light spot array formed on the sample and an axis of movement Lr of the rectilinear movement device projected on the sample stage is θ, the interval between light spots in the row direction is P1, and the interval between spots in the column direction is P2, the light spot array is formed with respect to the axis of movement Lr of the rectilinear movement device so that the following equation is satisfied:

$$\tan \theta = (1/n) \times (P1/P2)$$

Preferably, when the intervals P1 and P2 of the row direction and column direction between light spots of the light spot array formed on the sample are set so that P1=P2, the light spot array is formed with respect to the axis of movement Lr of the rectilinear movement device so that the following equation is satisfied:

$$\tan \theta = 1/n$$

Preferably, the sample stage moves rectilinearly by exactly a distance corresponding to a scan width while the sample stage rotates one time.

Preferably, a beam splitter is arranged in the light path between the light source and sample stage so as to separate the light beam heading from the light source to the sample stage and the light beam heading from the sample stage to the photosensor.

Preferably, an integrating interference optical system is arranged in the light path between the beam splitter and object lens.

Preferably, the integrating interference optical system is formed by a Nomarski prism.

Preferably, a zoom lens system is arranged in the light path between the photosensor and beam splitter.

Preferably, the array of light receiving elements of the photosensor is formed by an array of photodiodes separated by light blocking members.

Preferably, the defect detection circuit is connected to each light receiving element of the photosensor and has a comparison circuit for comparing an output signal of a light receiving element with a reference lower limit.

Preferably, the defect detection circuit is connected to each light receiving element of the photosensor, has a first comparison circuit for comparing an output signal of a light receiving element with a reference lower limit and a second comparison circuit for comparing it with a reference upper limit, and generates a defect detection signal when the output signal of the light receiving element exceeds the reference lower limit or reference upper limit.

The defect detection circuit is provided with a first line of OR circuits having m' number of OR circuits arranged along a row direction and a second line of OR circuits having n' number of OR circuits arranged along a column direction, an output of the comparison circuit connected to the i×j light receiving elements is connected to an i-th OR circuit of the first line of OR circuits and a j-th OR circuit of the second line of OR circuits, and a light receiving element detecting a defect is specified from the output signals of the first and second lines of OR circuits.

Preferably, the photosensor and defect detection circuit are formed integrated on a single chip.

Preferably, the sample stage has a θ-stage able to rotate around an axis of rotation and an r-stage able to move along the axis of movement Lr, a first position detection device for detecting an angular position in a rotational direction is connected to the θ-stage, and a second position detection device for detecting a position in a direction of an axis of rectilinear movement is connected to the r-stage.

A system preferably is further provided with a defect address circuit for specifying an address of a defect using a defect signal generated from the defect detection circuit and positional signals supplied from the first and second position detection apparatuses.

Preferably, the sample to be inspected for defects is a semiconductor wafer not formed with any semiconductor devices.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Preferred embodiments of the present invention will be described in detail below while referring to the attached figures.

Figure 1:
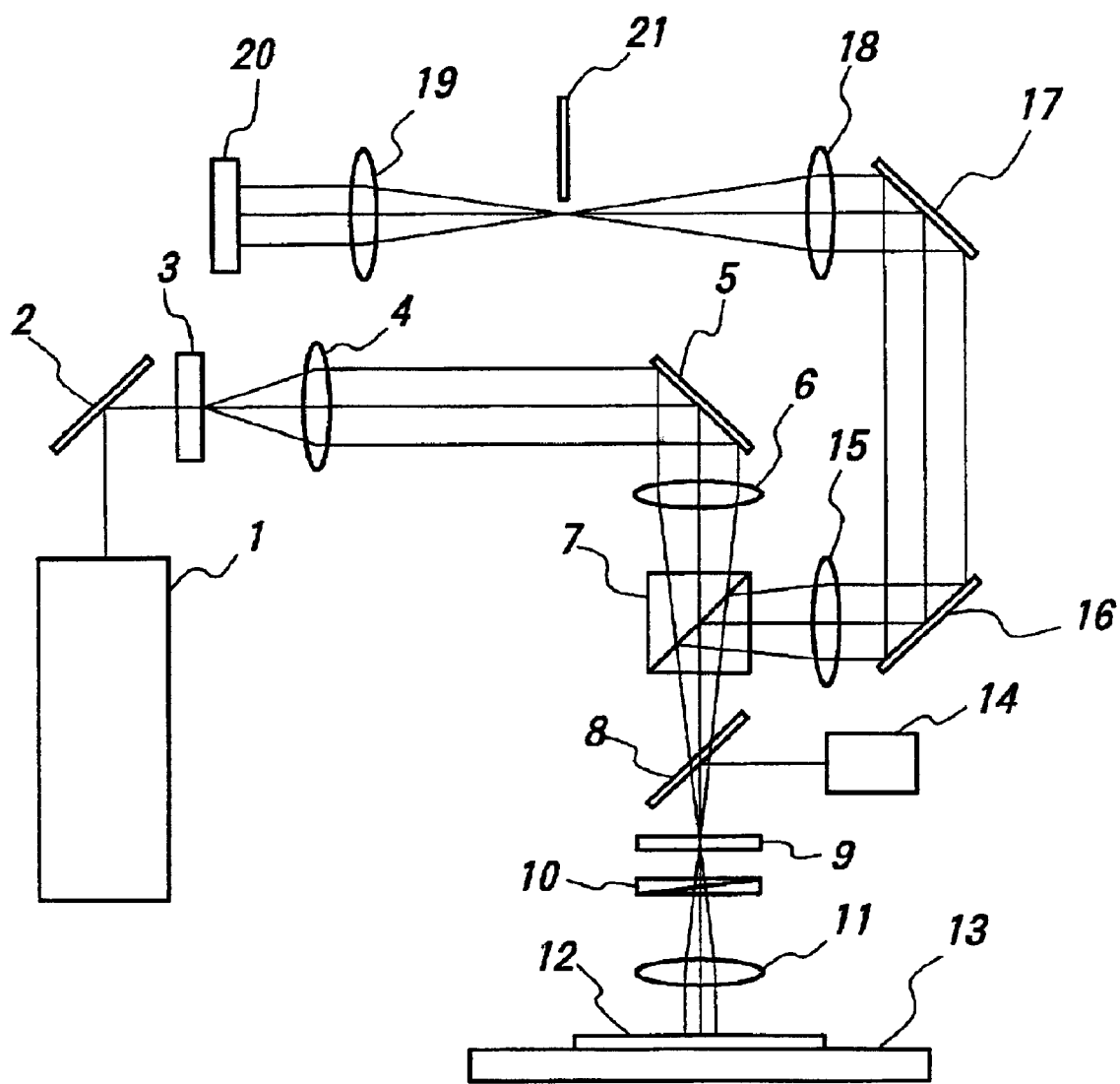
FIG. 1 is a schematic view showing the configuration of an example of an optically scanning apparatus according to the present invention.
Figure 2:
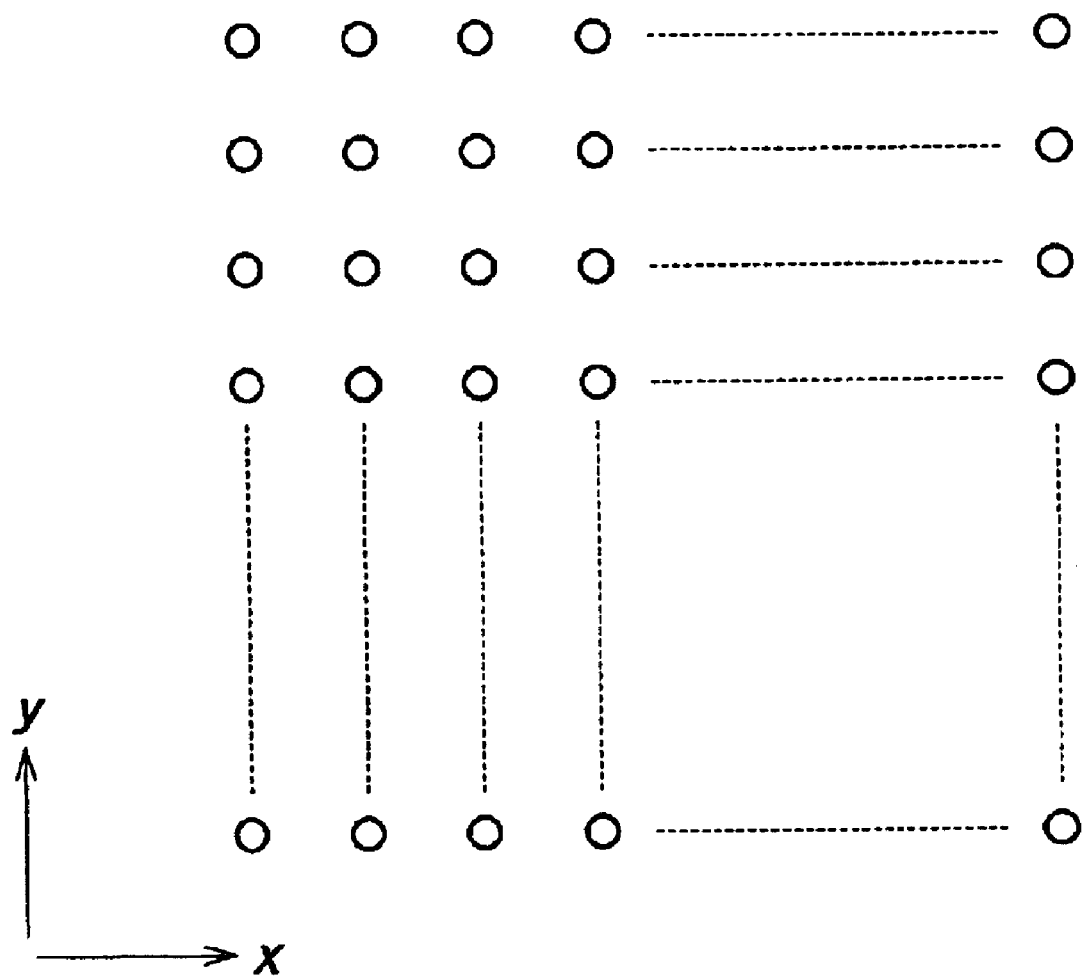
FIG. 2 is a schematic view illustrating an example of a beam array emitted from a two-dimensional diffraction grating.

FIG. 1 is a schematic view showing an embodiment of an optically scanning apparatus according to the present invention. In this example, as a light source 1, use is made of a YAG laser generating laser light of a wavelength of for example 532 nm. The beam emitted from the laser source 1 is reflected by a full reflection mirror 2 and strikes a diffraction grating 3. The diffraction grating 3 is comprised of a two-dimensional diffraction grating. The striking light beam is converted to a two-dimensional beam array of m×n number of light beams (m and n being natural numbers of 2 or more). In this example, a single light beam is used to generate a 33×33 two-dimensional beam array. FIG. 2 is a view of the converted beam array projected on a plane perpendicularly intersecting the light axis. The m×n number of light beams form a two-dimensional beam array comprised of light beams separated by equal intervals in the x and y directions. In this example, as the two-dimensional diffraction grating, it is also possible to use a hologram type diffraction grating or a two-dimensional diffraction grating comprised of two one-dimensional diffraction gratings arranged to intersect each other perpendicularly.

The m×n number of light beams strike the full reflection mirror 5 via a Fourier transform lens 4 and strike a polarization beam splitter 7 via a relay lens 6. This polarization beam splitter 7 acts to separate the light beam propagating from the light source to the sample and a light beam propagating from the sample to the photosensor. The light beams passing through the polarization beam splitter 7 passes through a dichroic mirror 8 and strikes an objective lens 11 through a λ/4 plate 9 and a Nomarski prism 10. This Nomarski prism 10 functions as a differential interference optical system. By arranging such interference optical system between the beam splitter and the objective lens 11, the accuracy of detecting defects can be improved. The light beams are focused to fine spots by the objective lens 11 and strike the sample 12 to be inspected for defects. Therefore, an m×n matrix light spot array is formed on the surface of the sample 12.

In this example, the sample 12 to be inspected for detects is a semiconductor wafer not formed with semiconductor devices, that is, a wafer blank. The sample 12 is placed on a sample stage 13. The sample stage 13 is a θ-r stage having a rotational drive mechanism and a rectilinear drive mechanism for rectilinear movement in a direction perpendicular to the axis of rotation. The rotational speed of the θ-r stage and the speed of movement in the r direction freely adjustable. During scanning, the sample stage 13 is rotated and moved rectilinearly, so the sample 12 is scanned spirally by the 33×33 light beam array. When the surface of the sample 12 has micro foreign matter, scratches, step differences, or film-like foreign matter, the striking light beams are randomly reflected or scattered by these defects. This randomly reflected light or scattered light is off from the light path reaching the photosensor, so it is possible to detect defect information due to foreign matter or scratches on the surface of the sample by detecting the regularly reflected light from the surface of the sample.

The reflected beams regularly reflected at the surface of the sample 12 are condensed by the objective lens 11 and strike the dichroic mirror 8 via the Nomarski prism 10 and the λ/4 plate 9. Part of the reflected light is reflected at the dichroic mirror and strikes an automatic focusing system 14. This automatic focusing system 14 has a light source generating a light beam of a wavelength different from the wavelength of the scan beam. This light beam is projected on the sample through the dichroic mirror 8. The light reflected from the sample is received through dichroic mirror 8. The automatic focusing system is known. In this example, an optical lever type automatic focusing system is used. As an automatic focusing system other than the optical lever type, it is possible to, for example, use a focus adjusting system utilizing the astigmatic method. It is possible to use the output signal of the automatic focusing system 14 to adjust the distance of the objective lens 11 to the sample 12. Further, it is possible to use a half mirror instead of the dichroic mirror and use part of the scan beam as the light beam for the automatic focusing system.

The reflected light beams passing through the half mirror 8 strike the polarization beam splitter 7. These passes through the λ/4 plate 9 two times, so the polarizing plane is rotated 90 degrees. As a result, the light is reflected at the polarizing plane of the beam splitter 7 and is separated from the light beam traveling from the light source to the sample. The light beam reflected at the polarization beam splitter 7 travels via the relay lens 15, the full reflection mirrors 16 and 17, and the relay lenses 18 and 19 to strike the photosensor 20. A spatial filter 21 is arranged at the pupil position between the relay lens 18 and a zoom lens system 19. The spatial filter 21 can be configured by a light blocking plate blocking one half of the optical path in a direction corresponding to the scan direction of the light spots on the sample.

Figure 3:
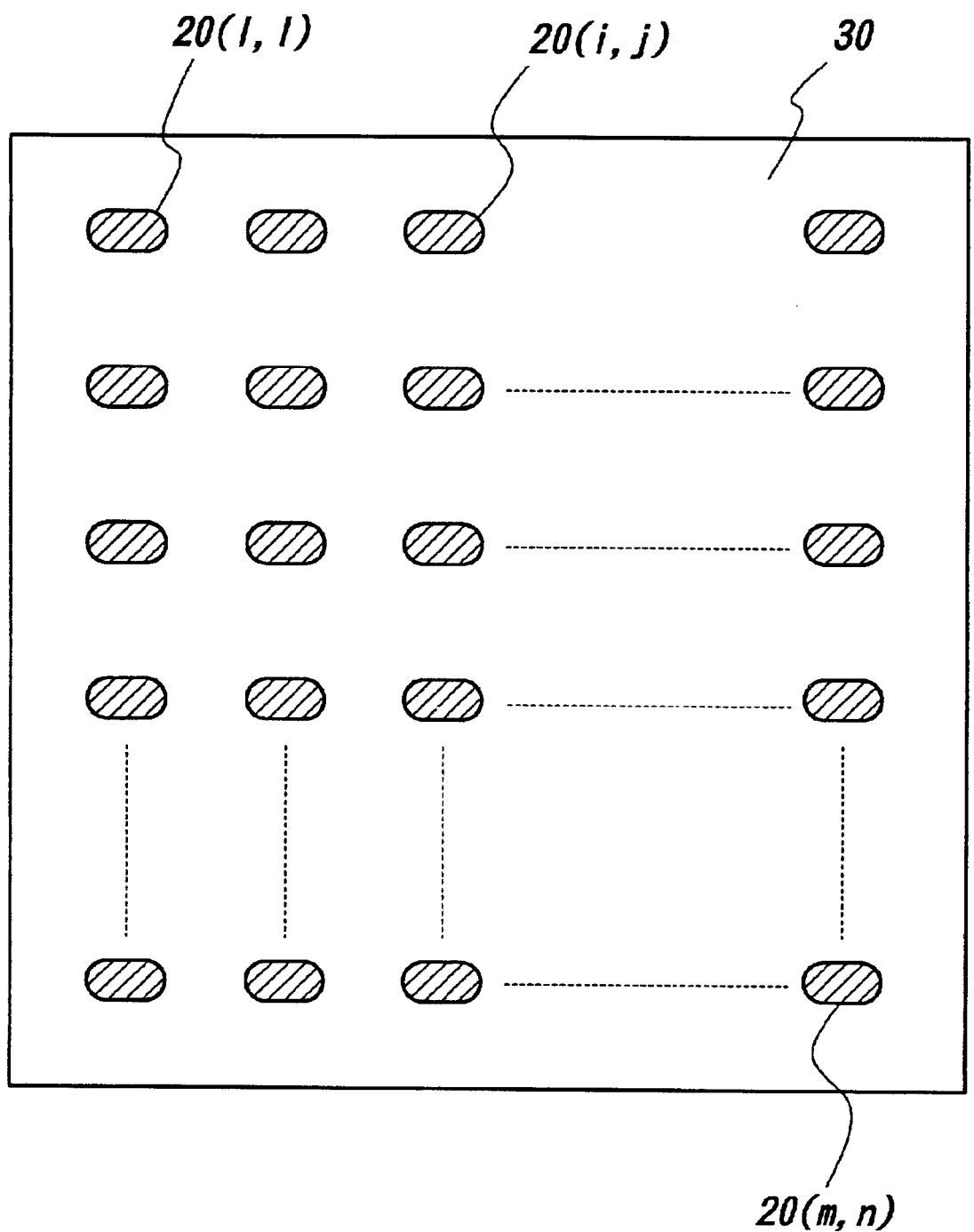
FIG. 3 is a schematic view illustrating the configuration of an example of a photosensor.

FIG. 3 is a schematic view showing the configuration of an example of a photosensor. The photosensor 20 has a two-dimensional matrix type light receiving element array 20 comprised of light receiving elements formed at equal intervals along a row and column direction. The light receiving elements receive the light regularly reflected from the corresponding light spots formed on the sample. The light receiving elements are comprised of photodiodes and are separated from each other by light blocking members 30. The regions of the light receiving elements struck by the light reflected from the sample are defined by the light blocking members 30 so that only the substantially regularly reflected light of the corresponding light spots formed on the surface of the sample strike them. As a result, the optical system of this example forms a confocal optical system and a much higher resolution can be obtained.

The relay lens 19 arranged at the front of the photosensor 20 is comprised by a zoom lens system. By adjusting the magnification of the zoom lens system, it is possible to make the beams reflected from the sample reliably strike the corresponding light receiving elements of the photosensor. For example, even when there is manufacturing error in an optical component, by adjusting the magnification of the zoom lens system, it is possible to make the light reflected from the light spots formed on the sample strike the corresponding light receiving elements.

Next, an explanation will be given of the scanning of the surface of the sample by a spot array. In the present invention, the above optical system is fixed in position and the sample stage made to move relatively with respect to the optical system to scan substantially the entire surface of the sample. In the present invention, as the relative movement of the sample stage with respect to the optical system, use is made of rotational movement of the stage and rectilinear movement in the radial direction (r direction) in the plane of rotation. That is, the surface of the sample is spirally scanned by making the stage move in the radial direction while making the stage rotate.

Figure 4:
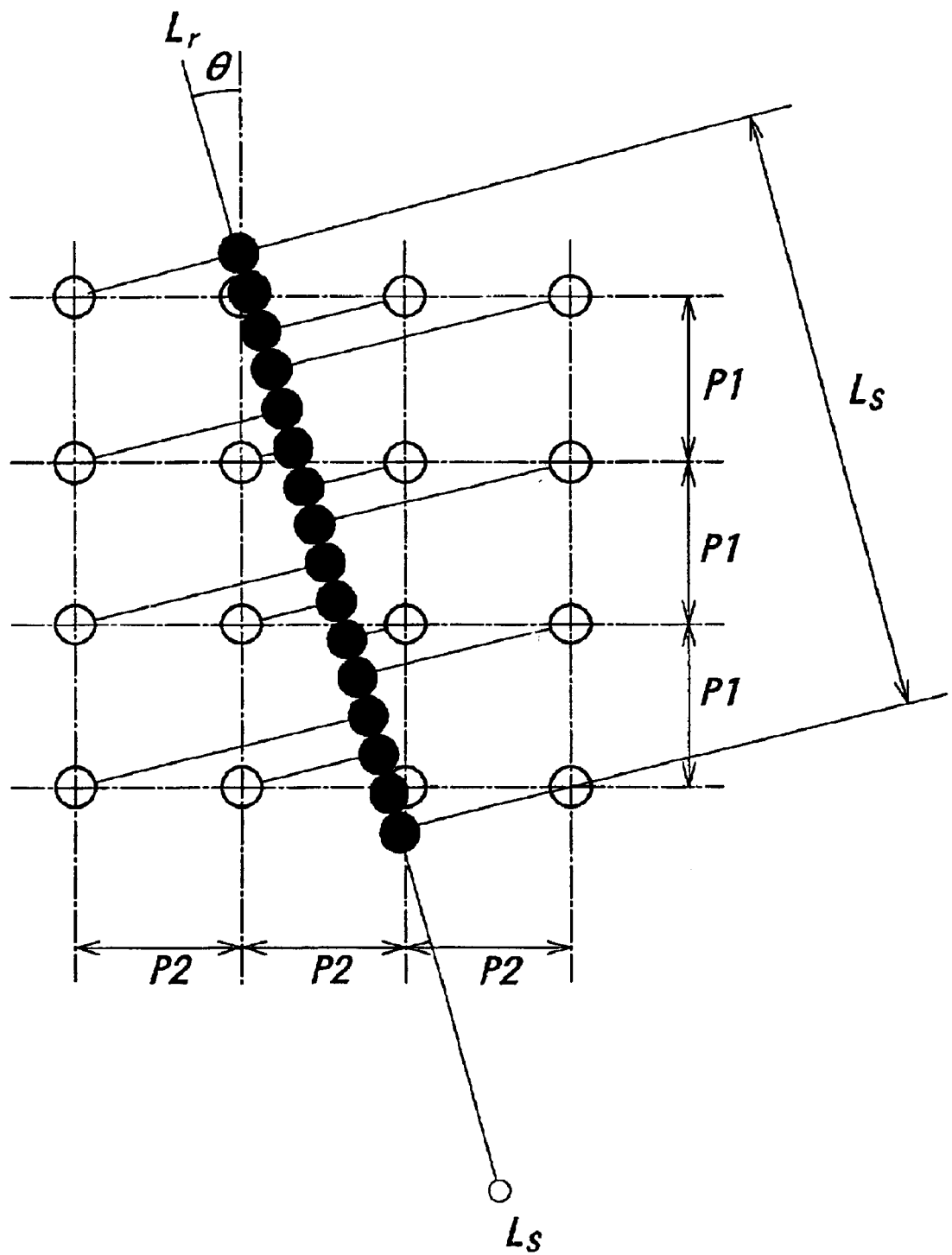
FIG. 4 is a schematic view illustrating a projection of a 4×4 array of light spots on an axis of rectilinear movement.

FIG. 4 shows the r direction axis of movement Lr and projection of the light spot array on the sample and projections of the light spots on the r direction axis of movement Lr. To clarify the drawing, a 4×4 light spot array is shown. The interval of the light spots of the light spot array in the row direction is made P1, while the interval in the column direction is made P2. To scan the surface of the sample by the m×n light spot array without gaps, it is necessary that the projections of the light spots with respect to the r direction axis of movement Lr be formed at equal intervals. The conditions for this will be explained next. The angle formed by the axis of the light spot array in the row direction and the r direction axis of movement Lr is made θ. The projected length of the intervals P1 between light spots in the row direction with respect to the r direction axis of movement becomes P1×cos θ. It is necessary that the projections of the n number of light spots in the column direction be present in the projected length. This condition can be expressed by P1×cos θ=n×P2×sin θ. Therefore, when the following equation is satisfied:

$$\tan \theta = (1/n) \times (P1/P2) \qquad (1)$$

projections of the light spots of the m×n light spot array with respect to the r direction axis of movement Lr are formed at equal intervals. When the intervals of the light spots in the row and column directions are equal (P1=P2), the light spot array is formed with respect to the r direction axis of movement Lr to satisfy the following equation:

$$\tan \theta = 1/n \qquad (2)$$

FIG. 4 shows the light spot array when the condition of equation (2) is satisfied. The white dots show the light spots formed on the sample, while the black dots show projections of the light spots on the r direction axis of movement Lr.

Figure 5:
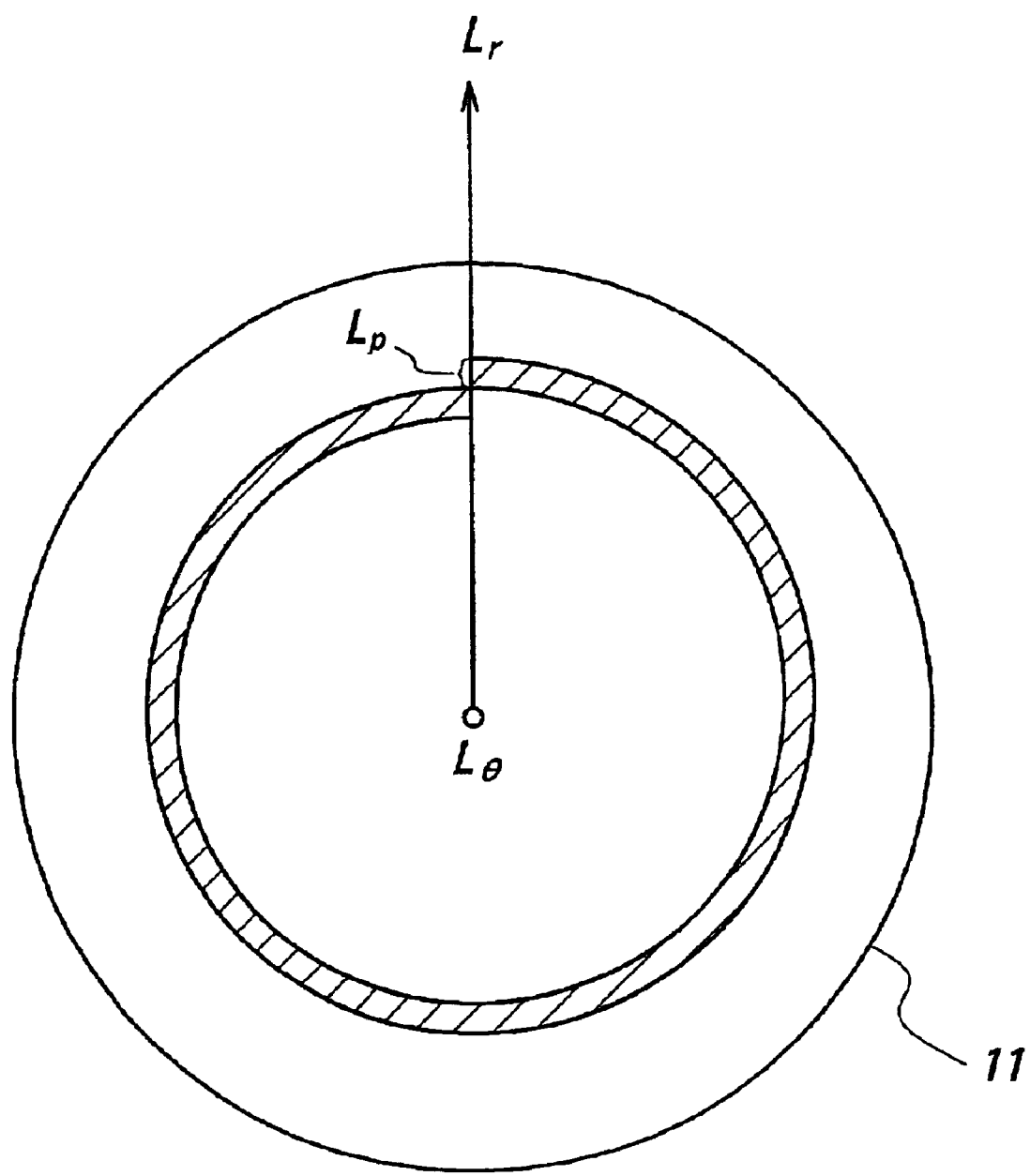
FIG. 5 is a schematic view showing the path of a spiral scan when scanning the surface of a sample using a two-dimensional array of light spots.

Next, an explanation will be given of the state of scanning the surface of a sample by a light spot array through the rotation and rectilinear movement of the sample stage. During the defect detection operation, since the optical system is fixed and the stage rotates and moves rectilinearly in the radial direction as well, the sample is spirally scanned by the width of the full projected length Lp (shown in FIG. 4) with respect to the axis of movement Lr of the light spot array (in this specification, called the "scan width"). This state is shown by a schematic view in FIG. 5. Here, when scanned by the m×n light spot array, the full projected length Lp can be expressed by Lp=m×P1×cos θ. In the present invention, the amount of movement of the stage in the radial direction during the period of one rotation of the stage is set to become equal to the full projected length Lp with respect to the axis of movement Lr of the light spot array. By configuring the apparatus in this way, it is possible to scan a sample without gaps and without overlap of light spots.

Figure 6A:
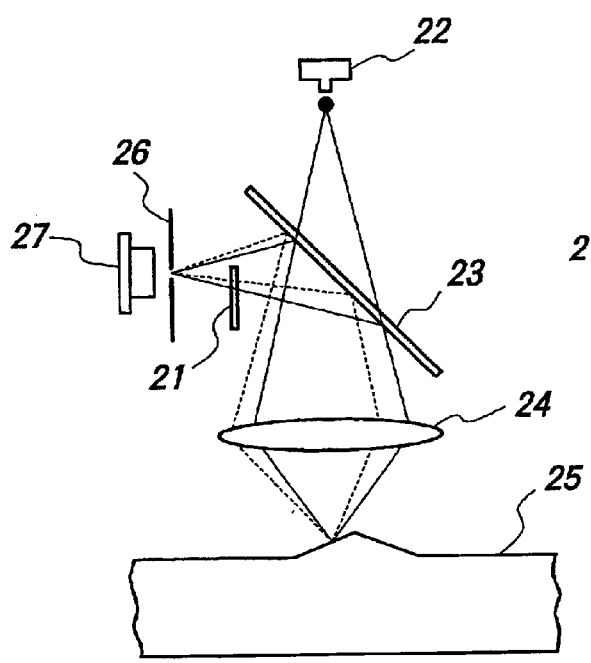
FIGS. 6A and 6B are schematic views for explaining the action of a spatial filter.
Figure 6B:
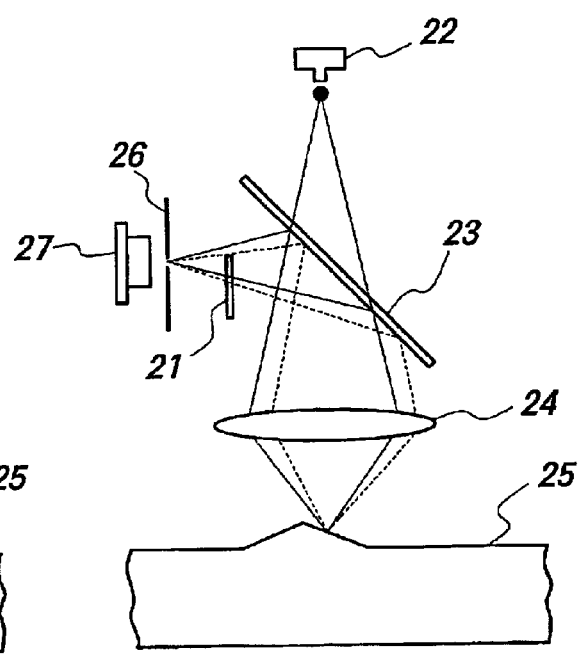
Figure 7:
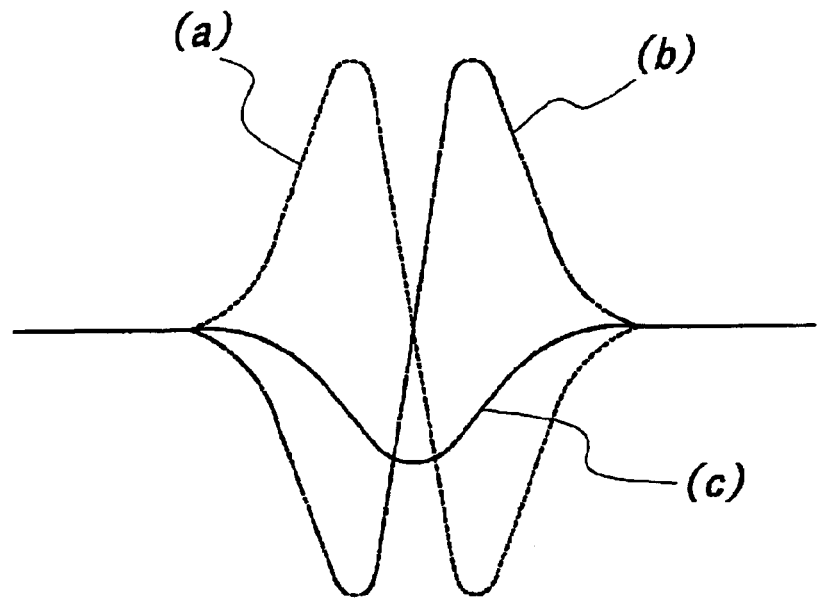
FIG. 7 is a view of waveforms of output signals from a light receiving element when a spatial filter is present in the light path and when it is not present there.

Next, an explanation will be made of the action of the spatial filter 21. The spatial filter 21 is comprised of a light blocking plate for blocking substantially one half of the optical path at the pupil position in the direction of rotational movement of the sample on the sample stage, that is, the direction corresponding to the scan direction by the light spots. When the surface of the sample is a smooth flat surface, the regularly reflected light from the surface of the sample propagates directly along the center of the optical path. When the surface of the sample has gently changing unevenness, however, the regularly reflected light from the inclined surface dose not propagate along the optical path in parallel to the optical axis and advances by a slight angle with respect to the light axis. Therefore, by arranging the light blocking plate 21 blocking one side of the light path at the pupil position, the amount of the regularly reflected light from the inclined portion of the surface of the sample which is blocked changes by a large extent. This state is schematically shown in FIGS. 6A and 6B. FIG. 6A shows the illumination light from the light source 22 reflected at the projecting inclined surface of the sample surface 25 through the half mirror 23 and the objective lens 24. FIG. 6B shows the light reflected at a recessed inclined surface of the sample surface 25. In the case of a projecting inclined surface, as shown in FIG. 6A, the amount of light blocked by the light blocking plate 21 is reduced, so the amount of light striking the light receiving elements 27 through another spatial filter 26 having pinholes is increased compared with the reflection at a smooth surface. On the other hand, in the case of a recessed inclined surface, the amount of light blocked by the light blocking plate 21 increases, so the amount of light striking the light receiving elements 27 is reduced. The wave-form of the output signal of a light receiving element in this case is schematically shown in FIG. 7. In FIG. 7, the solid line shows the waveform of an output signal of a light receiving element when there is no light blocking plate, the curve (a) shows the waveform of an output signal of a light receiving element when there is a projecting defect, and curve (b) shows the waveform of an output signal when there is a recessed defect. When there is a projecting defect, the substrate surface gradually becomes higher, peaks, then gradually becomes lower. As a result, the detected signal waveform, as shown by the curve (a) of FIG. 7, has a positive peak and then a negative peak. On the other hand, in the case of a recessed defect, as shown by the curve (b) of FIG. 7, first a negative peak occurs, then a positive peak occurs. As opposed to this, when there is no spatial filter in the light path, as shown by the curve (c), just a gently changing negative peak occurs. In this way, by just positioning the light blocking plate 20 in front or in back of the scan direction of the sample surface, it is possible to determine projecting defects and recessed defects from the output signals of the light receiving elements. Further, the sensitivity of detection of the defects also becomes greater.

Figure 8:
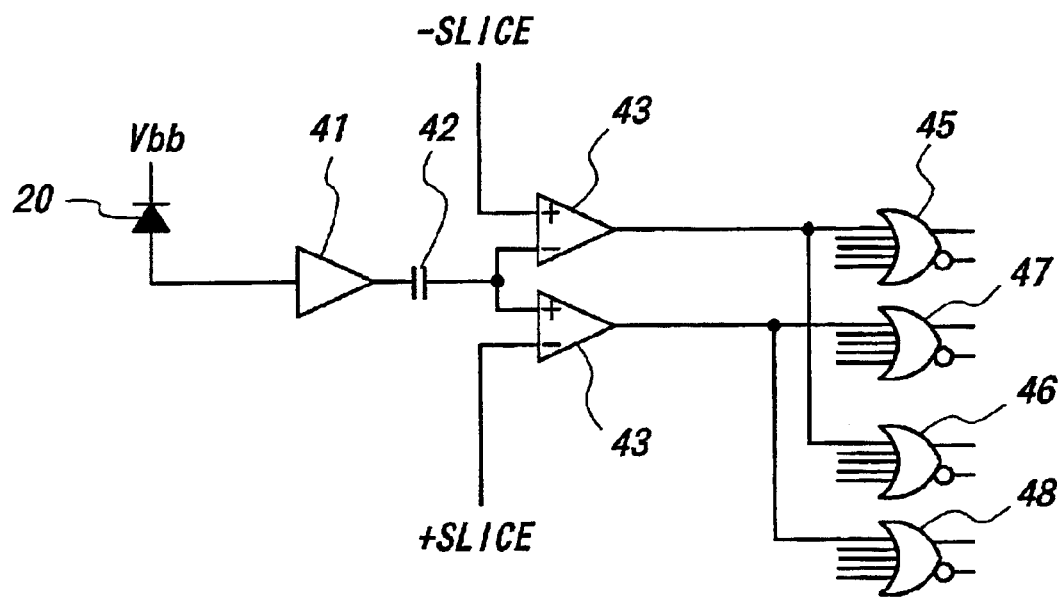
FIG. 8 is a schematic view showing the configuration of an example of a defect detection circuit of one channel.

Next, an explanation will be made of the defect detection circuit. FIG. 8 is a circuit diagram showing the configuration of one example of a defect detection circuit. As explained based on FIGS. 6A and 6B and FIG. 7, when a light beam scans over a defect present on the sample surface, if there is a projecting defect, the intensity of the output signal from that light receiving element gradually increases then gradually decreases. Further, if there is a recessed defect, the intensity of the output signal of the light receiving element gradually decreases, then increases. Therefore, by detecting if the intensity of an output signal from a light receiving element exceeds an upper and lower threshold value, projecting and recessed defects can be detected. Further, in the case of a defect due to deposition of foreign matter, since the amount of the regularly reflected light greatly decreases, it is possible to detect a defect by whether the output signal of a light receiving element exceeds a predetermined threshold.

It is assumed that a defect detection circuit is connected to each light receiving element of the photosensor 20. FIG. 8 shows just the defect detection circuit of one channel. An amplifier 41 is connected to a light receiving element 20 comprised by a photodiode. The output of the amplifier 31 is connected to first and second comparators 43 and 44 through a capacitor 42. A minus slice voltage is applied to one input terminal of the first comparator 43 and whether the regularly reflected light from the sample striking the light receiving element exceeds a lower threshold is determined. A plus slice voltage is applied to one input terminal of the second comparator 44 and whether the regularly reflected light from the sample striking the light receiving element exceeds an upper threshold is determined. The first and second comparators 43 and 44 generate pulse signals when the amplified output signal from the light receiving element exceeds the predetermined thresholds. The output part of the first comparator 43 is connected to the first and second OR circuits 45 and 46, while the output of the second comparator 34 is connected to the third and fourth OR circuits 47 and 48. A defect detection signal is generated from the output of these OR circuits.

When the spatial filter 21 is not arranged in the light path, if the light beam scans a defect portion of a sample, as shown by curve (c) of FIG. 7, the amount of light striking the light receiving element is just reduced from the case of scanning a normal portion. Therefore, when not using a spatial filter 21, use is made of just a comparator detecting whether an output signal of a light receiving element exceeds a lower threshold value.

Figure 9:
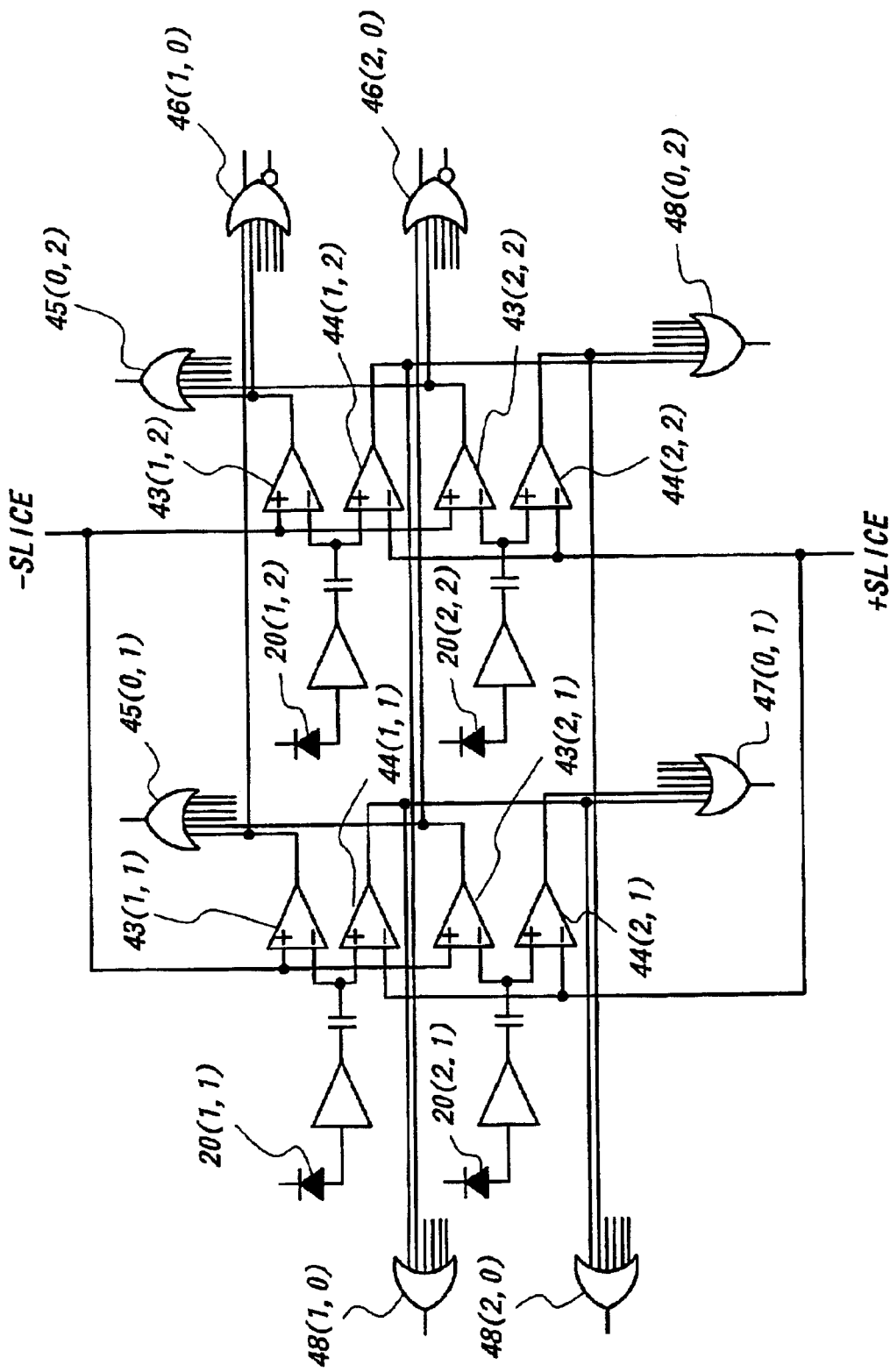
FIG. 9 is a circuit diagram showing the configuration of one example of an address circuit.

Next, an explanation will be given of the detection of the address of a defect. In this example, 31×31 light receiving elements and defect detection circuits are arranged in an i×j matrix. The elements are specified by (i,j). FIG. 9 shows the circuit configuration of the light receiving elements and defect detection circuits shown in FIG. 8 arranged in a 2×2 matrix. The output of a first comparator 43 for representing if the intensity of the output signal of a light receiving element exceeds a lower threshold value is connected to first and second OR circuits 45(i,0) and 46(0,j) arranged at each row and each column, respectively. Here, i is a whole number of $1 \leq i \leq 31$, while j is made a whole number of $1 \leq 1 \leq 31$. Similarly, the output of a second comparator 44 for representing if the intensity of the output signal of a light receiving element exceeds an upper threshold value is connected to third and fourth OR circuits 47(i,0) and 48(0,j) arranged at each line and each column, respectively. By arranging the light receiving elements and defect detection circuits in an i×j matrix in this way, it is possible to specify the address of a light receiving element detecting a defect based on the defect detection signals from the (o,i) OR circuit and (j,0) OR circuit when an (i,j) light receiving element detects a defect.

Figure 10:
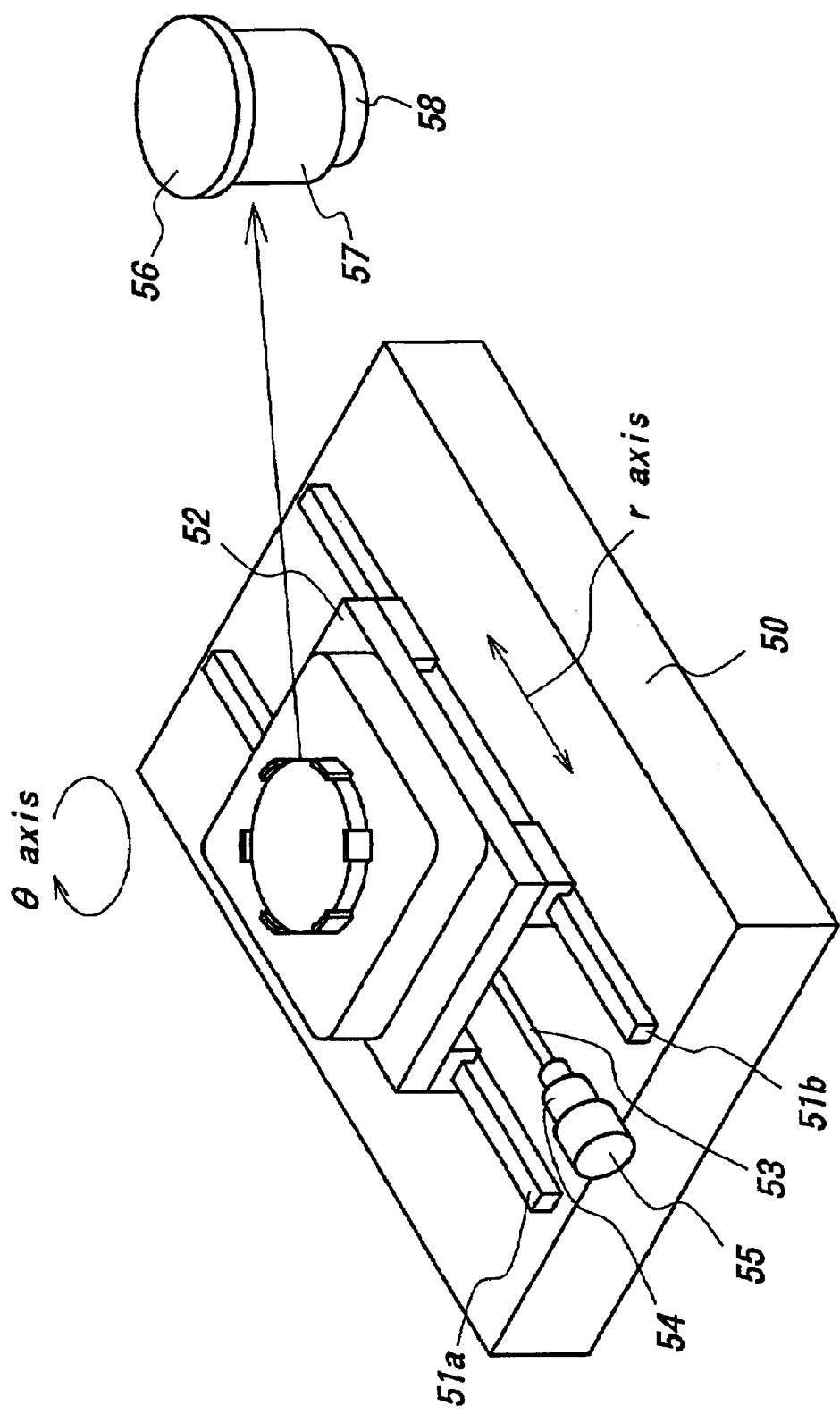
FIG. 10 is a perspective view showing the configuration of an example of a sample stage.

Next, an explanation will be given of the structure of the sample stage. FIG. 10 is a perspective view showing the configuration of an example of a sample stage. The sample stage has a base stage 50 and is provided with two linear guides 51a and 51b on the base stage 50. A r-stage 52 is slidably placed on the linear guides 51a and 51b. A ball screw 43 is connected to the r-stage. The ball screw has connected to it an r direction drive servo motor 54 and encoder 55 for detecting the position in the r direction. Further, the servo motor 54 is connected to a drive circuit (not shown). A θ-stage 56 is rotatably provided on the r-stage 52. The θ-stage 56 has connected to it a drive motor 57 and a rotary encoder 58 for detecting the position in the θ direction. The drive motor 57 is connected to a drive circuit (not shown). The sample to be inspected for defects is fixed on the θ-stage 56 by a chuck mechanism.

Figure 11:
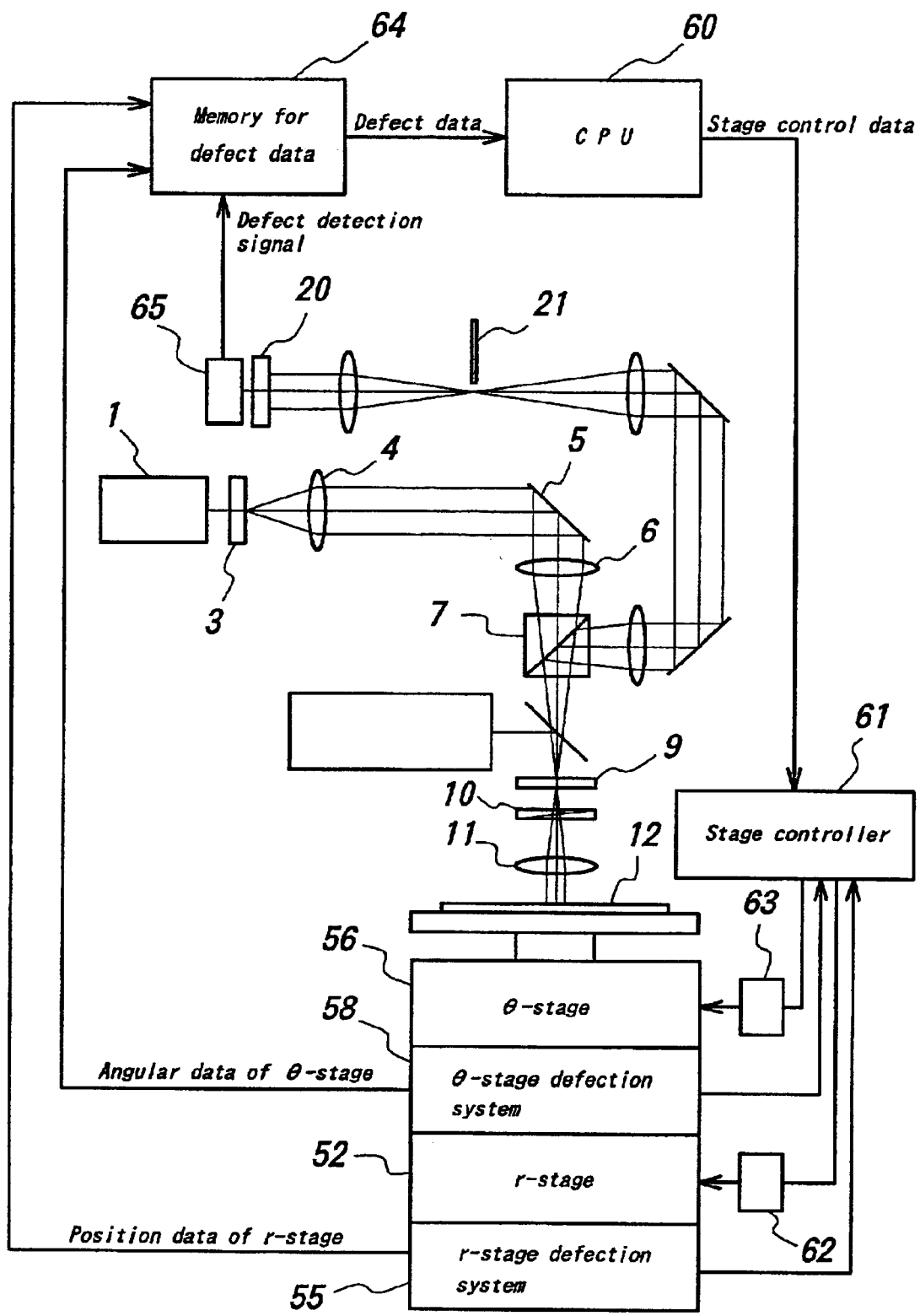
FIG. 11 is a schematic view showing drive control of a sample stage and control of address detection of defects.

FIG. 11 shows the configuration for detection of a defect address including the optical system shown in FIG. 1 by a line drawing. The drive control of the sample stage and control of address detection of defects are executed by a central processing unit (CPU) 60. The CPU 60 has a stage controller 61 connected to it. The stage controller 61 supplies an r-stage drive signal through an r-stage drive circuit 62 and a θ-stage drive signal through a θ-stage drive circuit 63. The r direction positional signal detected by the r stage position detection apparatus 55 and θ direction angular position detection signal detected by the θ-stage position detection apparatus 58 are supplied to the stage controller 61. The stage controller 61 uses the detected r direction and θ direction positional signals to generate r direction and θ direction drive control signals. Further, the r direction and θ direction positional signals are supplied to a defect data memory 64 storing the address information of defects and functioning also as a defect address circuit for specifying the address of a detected defect. The defect detection signal generated from the defect detection circuit 65 formed integrally with the photosensor 20 is also supplied to the defect data memory 64. Therefore, the defect data memory 64 specifies the address of a detected defect based on the two positional signals relating to the sample stage and the signal specifying the light receiving element detecting the defect and stores the specified defect address.

While the invention has been described with reference to specific embodiments chosen for purpose of illustration, it should be apparent that numerous modifications could be made thereto by those skilled in the art without departing from the basic concept and scope of the invention.

For example, in the above embodiment, the explanation was given with reference to the example of optically scanning a semiconductor wafer, but the invention can also be applied to an apparatus scanning a storage medium such as an optical disk or magneto-optic disk. In this case, if use is made of for example a 3×3 two-dimensional beam array, it is possible to simultaneously scan nine tracks at one time and possible to write information stored or read information written at a high speed.

In the above explanation, the defect detection circuit was configured to generate a defect detection signal using a comparison circuit comparing the intensity of an output signal of a light receiving element with a reference threshold value, but it is also possible to use various other defect detection methods. For example, it is possible to detect defects by comparing output signals of adjoining light receiving elements.

What is claimed is:

1. An optically scanning apparatus comprising:
a light source for emitting a radiation beam;
a two-dimensional diffraction grating for converting said radiation beam into a two-dimensional array of light beams arranged in an m×n matrix, where m and n are natural numbers of 2 or more;
an objective lens for focusing the m×n number of light beams into spots to form an array of light spots arranged in an m×n matrix on a sample to be inspected;
a photosensor having an array of light receiving elements arranged in an m'×n' (m' and n' being natural numbers of 2 or more) matrix, the light receiving elements separated from each other and receiving beams reflected at the sample surface;
a sample stage for supporting a sample to be inspected for defects; and
a stage drive system having a rotational drive device for rotating said sample stage and a rectilinear movement device for moving the sample stage along an axis perpendicular to the rotational axis and making said sample stage move relative to said light spot array;
wherein the sample surface is scanned by the two-dimensional light spot array arranged in an m×n matrix by making the sample and light spot array move relative to each other, and the sample surface is spirally scanned by the two-dimensional light spot array, and said sample stage moves rectilinearly by exactly a distance corresponding to a scan width while the sample stage rotates one time.

2. An optically scanning apparatus as set forth in claim 1, wherein the light spot array is formed so that the intervals between adjoining light spots become equal when projecting the m×n number of light spots formed on said sample on an axis of movement Lr of the rectilinear movement device projected on the sample stage.

3. An optically scanning apparatus as set forth in claim 2, wherein when an angle formed between an axis in a row direction of an m×n two-dimensional light spot array formed on said sample and an axis of movement Lr of the rectilinear movement device projected on said sample stage is θ, the interval between light spots in the row direction is P1, and the interval between spots in the column direction is P2, the light spot array is formed with respect to the axis of movement Lr of the rectilinear movement device so that the following equation is satisfied:

$$\tan \theta = (1/n) \times (P1/P2).$$

4. An optically scanning apparatus as set forth in claim 3, wherein when the intervals P1 and P2 of the row direction and column direction between light spots of the light spot array formed on the sample are set so that P1=P2, the light spot array is formed with respect to the axis of movement Lr of the rectilinear movement device so that the following equation is satisfied:

$$\tan \theta = 1/n.$$

5. An optically scanning apparatus as set forth in claim 1, wherein a beam splitter is arranged in the light path between the light source and sample stage so as to separate the light beam propagating from the light source to the sample stage and the light beam heading from the sample stage to the photosensor.

6. An optically scanning apparatus as set forth in claim 5, wherein an differential interference optical system is arranged in the optical path between the beam splitter and objective lens.

7. An optically scanning apparatus as set forth in claim 6, wherein said differential interference optical system is formed by a Nomarski prism.

8. An optically scanning apparatus as set forth in claim 5, wherein a zoom lens system is arranged in the optical path between said photosensor and beam splitter.

9. An optically scanning apparatus as set forth in claim 1, wherein the array of light receiving elements of said photosensor is formed by an array of separated photodiodes.

10. An optically scanning apparatus as set forth in claim 1, wherein said sample stage has a θ-stage able to rotate around an axis of rotation and an r-stage able to move along said axis of movement Lr, a first position detection device for detecting an angular position in a rotational direction is connected to the θ-stage, and a second position detection device for detecting a position in a direction of an axis of rectilinear movement is connected to the r-stage.

11. A defect inspection apparatus comprising:
a light source for emitting a radiation beam;
a two-dimensional diffraction grating for converting said radiation beam into a two-dimensional array of light beams arranged in an m×n matrix, where m and n are natural numbers of 2 or more;
an objective lens for focusing the m×n number of light beams into spots to form an array of light spots arranged in an m×n matrix on a sample to be inspected;
a photosensor having an array of light receiving elements arranged in an m'×n' (m' and n' being natural numbers of 2 or more) matrix, the light receiving elements separated from each other and receiving beams reflected at the sample surface;
a sample stage for supporting a sample to be inspected for defects; and
a stage drive system having a rotational drive device for rotating said sample stage and a rectilinear movement device for moving the sample stage along an axis perpendicular to the rotational axis and making said sample stage move relative to said light spot array; and
a defect detection system for detecting a defect present on a surface region of a sample based on an output signal from a light receiving element of said photosensor, wherein the sample surface is spirally scanned by the light spot array, and said sample stage moves rectilinearly by exactly a distance corresponding to a scan width while the sample stage rotates one time.

12. A defect inspection system as set forth in claim 11, wherein the two-dimensional diffraction grating converts the radiation beam into a two-dimensional beam array comprised of light beams arranged at equal intervals in a row direction and column direction.

13. A defect inspection system as set forth in claim 11, wherein the light spot array is formed so that the intervals between adjoining light spots become equal when projecting m×n number of light spots formed on said sample on an axis of movement Lr of the rectilinear movement device projected on the sample stage.

14. A defect inspection system as set forth in claim 12, wherein when an angle formed between an axis in a row direction of an m×n two-dimensional light spot array formed on said sample and an axis of movement Lr of the rectilinear movement device projected on said sample stage is θ, the interval between light spots in the row direction is P1, and the interval between spots in the column direction is P2, the light spot array is formed with respect to the axis of movement Lr of the rectilinear movement device so that the following equation is satisfied:

$$\tan \theta = (1/n) \times (P1/P2).$$

15. A defect inspection system as set forth in claim 14, wherein when the intervals P1 and P2 of the row direction and column direction between light spots of the light spot array formed on the sample are set so that P1=P2, the light spot array is formed with respect to the axis of movement Lr of the rectilinear movement device so that the following equation is satisfied:

$$\tan \theta = 1/n.$$

16. A defect inspection system as set forth in claim 11, wherein a beam splitter is arranged in the light path between the light source and sample stage so as to separate the light beam propagating from the light source to the sample stage and the light beam propagating from the sample stage to the photosensor.

17. A defect inspection system as set forth in claim 11, wherein a differential interference optical system is arranged in the light path between the beam splitter and objective lens.

18. A defect inspection system as set forth in claim 17, wherein said differential interference optical system is formed by a Nomarski prism.

19. A defect inspection system as set forth in claim 11, wherein a zoom lens system is arranged in the light path between said photosensor and beam splitter.

20. A defect inspection system as set forth in claim 11, wherein the array of light receiving elements of said photosensor is formed by an array of photodiodes separated by light blocking members.

21. A defect inspection system as set forth in claim 11, wherein said defect detection system comprises comparison circuits connected to each light receiving element of said photosensor and comparing the output signal of the light receiving element with a reference lower limit.

22. A defect inspection system as set forth in claim 11, wherein said defect detection system comprises a first and a second comparison circuit connected each light receiving element and comparing the output signal of the light receiving element with a reference lower limit and upper limit, respectively and generates a defect detection signal when the output signal of the light receiving element exceeds the reference lower limit or reference upper limit.

23. A defect inspection system as set forth in claim 21, wherein said defect detection system is provided with a first line of OR circuits having m' number of OR circuits arranged along a row direction and a second line of OR circuits having n' number of OR circuits arranged along a column direction, the output of the comparison circuit connected to the i×j light receiving elements is connected to an i-th OR circuit of the first line of OR circuits and a j-th OR circuit of the second line of OR circuits, and the light receiving element detecting a defect is specified from the output signals of the first and second lines of OR circuits.

24. A defect inspection system as set forth in claim 11, wherein said photosensor and defect detection circuit are formed integrated on a single chip.

25. A defect inspection system as set forth in claim 11, wherein said sample stage has a θ-stage able to rotate around an axis of rotation and an r-stage able to move along said axis of movement Lr, a first position detection device for detecting an angular position in a rotational direction is connected to the θ-stage, and a second position detection device for detecting a position in a direction of an axis of rectilinear movement is connected to the r-stage.

26. A defect inspection system as set forth in claim 11, further provided with a defect address circuit for specifying an address of a defect using a defect detection signal generated from said defect detection circuit and positional signals supplied from said first and second position detection apparatuses.

27. A defect inspection system as set forth in claim 11, where said sample to be inspected for defects is a semiconductor wafer not formed with any semiconductor devices.

* * * * *